United States Patent [19]

Sorce et al.

[11] 4,385,517

[45] May 31, 1983

[54] METHOD AND APPARATUS FOR MEASURING THE PERMEABILITY OF A MATERIAL

[75] Inventors: Peter S. Sorce, Tonawanda; Earl W. Clifford, Getzville, both of N.Y.

[73] Assignee: The Aro Corporation, Bryan, Ohio

[21] Appl. No.: 277,681

[22] Filed: Jun. 26, 1981

[51] Int. Cl.³ .......................................... G01N 15/08
[52] U.S. Cl. ....................................................... 73/38
[58] Field of Search ............................................ 73/38

[56] References Cited

U.S. PATENT DOCUMENTS

| | | | |
|---|---|---|---|
| 2,350,058 | 5/1944 | May | 73/38 |
| 2,755,660 | 7/1956 | Kammermeyer et al. | 73/38 |
| 2,861,451 | 11/1958 | Emmons | 73/38 |
| 3,248,930 | 5/1966 | Speegle et al. | 73/38 |
| 3,577,767 | 5/1971 | Stedile | 73/38 |
| 4,198,853 | 4/1980 | Graham et al. | 73/38 |

FOREIGN PATENT DOCUMENTS 1063832  8/1959  Fed. Rep. of Germany .......... 73/38

*Primary Examiner*—E. R. Kazenske
*Assistant Examiner*—Joseph W. Roskos
*Attorney, Agent, or Firm*—Sommer & Sommer

[57] ABSTRACT

Apparatus for measuring the permeability of a material to passage of a fluid includes a pressure regulator for varying the pressure of a supplied fluid, a pair of jaws which may be clamped onto the material specimen, a solenoid valve arranged between the regulator and the jaws, and a collapsible container arranged to be inflated with such fluid as may pass through the clamped specimen during the test. The permeability of the test specimen is determined in terms of the length of time needed for a known volume of such fluid to pass through the specimen, when fluid at a test pressure is applied to a unit area thereof. The apparatus may further include a pressure switch arranged to sense an inflated condition of the container, and a timer to disable the apparatus until sufficient time has been provided to enable the container to return to its deflated condition. In use, such apparatus performs an improved method of measuring the permeability of the material to passage of such fluid.

10 Claims, 3 Drawing Figures

0
METHOD AND APPARATUS FOR MEASURING THE PERMEABILITY OF A MATERIAL

BACKGROUND OF THE INVENTION

1. Field of the Invention

The present invention relates generally to the art of permeability testers, and more particularly to improved apparatus for measuring the permeability of sheet material to passage of a fluid.

2. Description of the Prior Art

The permeability of a material relates to the ability of a fluid, usually a liquid or gas, to pass through the material. Some materials are impervious, that is, unable to accommodate fluid penetration; others are pervious to some fluids, but impervious to others. There are many uses for pervious, semipervious, and impervious materials.

Surgical instruments are commonly stored in sterile packages. One face of the package is usually a transparent plastic; the other face may be a treated paper product. After the instrument has been sealed in the package, the entire package may be subjected to a suitable sterlizing gas, such as ethylene oxide. The plastic material is typically impervious to passage of both air and ethylene oxide. However, it is desired that the paper be pervious to ethylene oxide, but impervious to bacteria.

Devices for measuring the permeability of a material to a particular fluid have, of course, been heretofore developed. In one test, which appears to have been widely adopted in the industry, the permeability of a paper is measured in terms of the length of time needed for a volume of 100 cc of air, supplied at a pressure of 4.88 inches of water, to pass through 1.0 in$^2$ of the paper. Such paper is then commonly referred to as "twenty second paper", "twenty-seven second paper", and so forth. The industry-wide standards for such tests are currently embodied in ASTM Standard D726-58, entitled "Standard Methods of Test for Resistance of Paper to Passage of Air".

One device for measuring permeability is shown in Bulletin 1400, entitled "Paper Testing Instruments", by Teledyne Gurley, 514 Fulton St., Troy, N.Y. 12181. That brochure described the test apparatus as clamping 1.0 in$^2$ of paper, and supplying 100 cc of fluid (air) at a pressure of 4.88 inches of water. The air is supplied by a weighted cylinder floating in oil, and the volume is determined by the change in cylinder position. The "start" and "stop" points of such cylinder position may be measured electrically, as by two contact points, or photo-electrically. Upon study, however, it is felt that this apparatus provides numerous opportunities for human error, and therefore may be unreliable from a practical point of view. Moreover, it is believed that oil from the volumetric container may contaminate the test sample and invalidate the test.

SUMMARY OF THE INVENTION

The present invention provides a method and apparatus for measuring the permeability of a material to passage of a fluid.

The improved apparatus broadly includes: supply means for supplying a flow of fluid at a desired test pressure; clamp means including a pair of relatively-movable jaws between which a known area of the material specimen may be selectively clamped; valve means operatively arranged between the supply means and one of the jaws for selectively permitting the flow to be applied to one face of the material and for selectively interrupting the flow; collection means communicatively connected to the other of the jaws and operatively arranged to collect a known volume of such fluid as may pass through the specimen, sensing means operatively arranged to sense the presence of a desired volume of such fluid within the collection means, and timing means operatively arranged to sense the time interval needed to collect the desired volume of such fluid within the collection means.

In use, such apparatus performs an improved testing method, which broadly comprises the steps of: supplying a flow of fluid at a desired test pressure, applying this flow to a known area of the test specimen, collecting such fluid as may pass through the test specimen, and measuring the time interval needed to collect a desired volume of such collected fluid.

Accordingly, it is one general object of the present invention to provide improved apparatus for measuring the permeability of a material to passage of a fluid.

Another general object is to provide an improved method of measuring the fluid-permeability of a material.

Another object is to provide such improved apparatus, which is simple to operate and which incorporates a "fail-safe" time delay feature, which disables the apparatus until the collection device is ready for the next sequential test.

Another object is to provide such improved apparatus, in which the opportunity for the inadvertent injection of human errors is practically minimized.

These and other like objects and advantages will become apparent from the foregoing and ongoing written specification, the drawings, and the appended claims.

DESCRIPTION OF THE PREFERRED EMBODIMENTS

Figure 1:
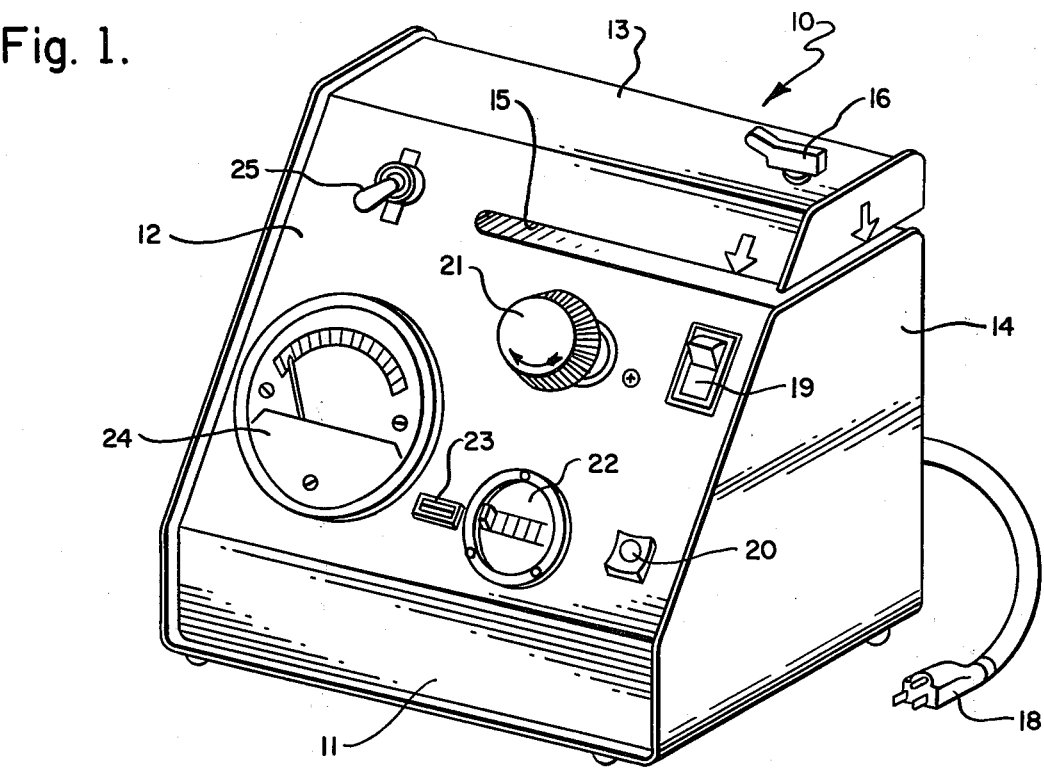
FIG. 1 is a perspective view looking at the right front corner of the improved apparatus.

At the outset, it should be clearly understood that like reference numerals are intended to identify the same elements and/or structure consistently throughout the several drawing figures, as such elements and/or structure may be further described or explained by the entire written specification of which this detailed description is an integral part.

Referring now to the several drawing figures, and more particularly to FIG. 1 thereof, the invention broadly provides improved apparatus, of which the presently-preferred embodiment is generally indicated at 10, for measuring the permeability of a material to passage of a fluid. In use, the inventive apparatus also performs as improved method of determining such permeability.

In FIG. 1, the improved apparatus 10 is provided with an enclosing cover, which includes a lower vertical front panel 11, an upwardly and rearwardly-inclined front panel 12, a horizontal top panel 13, a vertical right side panel 14, a back panel (not shown), a left side panel (not shown), and a bottom panel (not shown). The cover is shown as provided with a horizontal slot 15 which extends from the right side panel leftwardly for about sixty percent of the width of the front panel. A suitable cam-operated toggle mechanism 16 is mounted on cover top panel 13 for effecting selective movement of the movable jaw. If desired, a pneumatically-operated piston clamp, or some other remotely actuated device, may be substituted for toggle mechanism 16. The improved apparatus is adapted to be connected via plug 18 to a suitable power source. For typical use in the United States, the power source may be 110 V.A.C., 60 cycle. In other domestic or foreign applications, however, the power source may supply 220-240 V.A.C., 50 or 60 cycle, as required. However, the particular characteristics of the power source are not deemed critical, and these may be readily varied, as desired.

A number of controls and gauges are mounted on inclined front panel 12. These include: an on-off switch (preferably illuminated) 19; a push-type test activation switch 20; a rotatable knob 21 for use in adjusting the pressure supplied by a variable pressure regulator; a totalizing timer 22 with a manually-operable push reset feature; a "ready" indicator light 23; a pressure gauge 24; and a two-position toggle switch 25 selectively movable between "test" and "calibration" modes of operation. The improved apparatus is also supplied with pressurized fluid from a suitable source thereof (not shown).

As used herein, the term "fluid" is intended to mean either a liquid or gas. In the ensuing description, the fluid will be described as being air. However, it should be clearly understood that the term "fluid", as used herein, means gases other than air, as well as a variety of operable liquids. For example, if desired, the "fluid" may be ethylene oxide in order to determine the permeability of the test specimen to passage of that gas.

Figure 2:
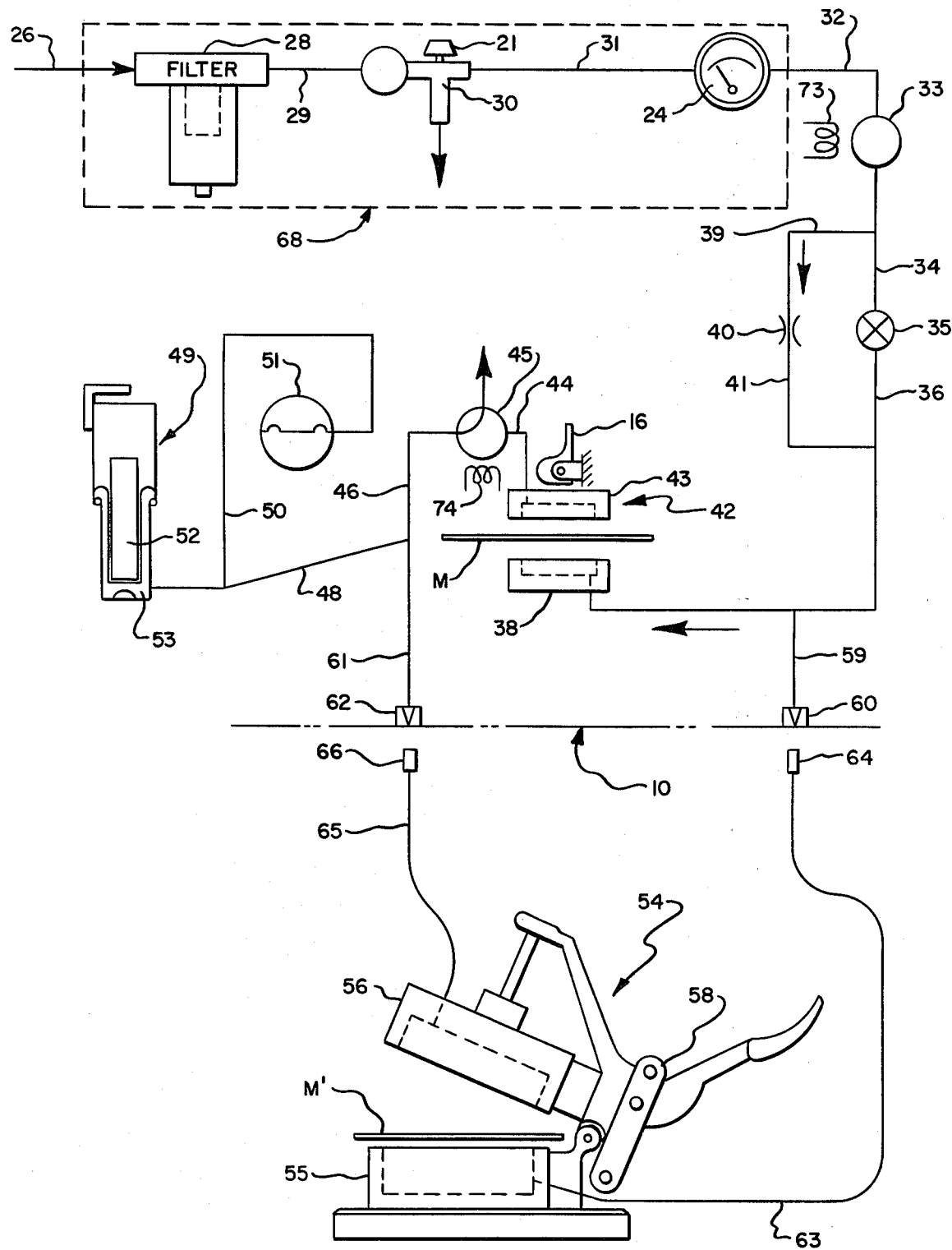
FIG. 2 is a schematic of the pneumatic circuitry thereof.

Referring now to FIG. 2, which illustrates a pneumatic schematic of the preferred embodiment, compressed air from a suitable source (not shown) is supplied via conduit 26 to a filter 28; thence, via conduit 29 to a variable pressure regulator 30, the operation of which is controlled by manual rotation of knob 21. Regulator 30 constantly bleeds air through a suitable orifice to atmosphere, so as to minimize fluctuation in the controlled pressure in downstream flow conduit 31 leading to pressure gauge 24. In the preferred embodiment, which uses an industry standard, knob 21 on pressure regulator 30 may be manipulated until gauge 24 indicates 4.88 inches of water. For convenience, gauge 24 may be calibrated in inches of water, pounds per square inch, or any other suitable unit of pressure. Conduit 32 leads from gauge 24 to an on-off two position solenoid valve 33. When closed, there is no flow through valve 33. When open, however, the regulated pressure flow is supplied through conduit 34, on-off valve 35 and conduit 36, to stationary lower jaw 38. Valve 35 is controlled by manipulation of toggle switch 25. A branch circuit includes: a conduit 39 communicating with conduit 34, a restricted orifice 40, and a conduit 41 communicating with conduit 36. When switch 25 is in the "calibrate" mode, valve 35 is closed so that flow through solenoid valve 33 will be diverted through the orifice. When valve 35 is open, conduits 34 and 36 are directly communicative. In the preferred embodiment, orifice 40 is configured to permit a flow of 100 cubic centimeters per minute at an indicated gauge pressure of 4.88 inches of water. This provides a means by which the operator can calibrate gauge 24, as hereinafter discussed.

The apparatus includes clamp means, generally indicated at 42, which includes stationary lower jaw 38, and an upper jaw 43 selectively movable toward and away from the lower jaw by means of cam-operated toggle linkage 16. Each jaw, 38 and 43, is shown as being a cup-shaped member arranged to face the other, and has a cylindrical side wall. The cross-sectional area enclosed within the side wall is, in the case of the preferred embodiment 1.0 in$^2$, although this may be varied as desired. The marginal end portions of the jaws may include a resilient gasket (not shown), which will inhibit radial leakage of the test fluid. Thus, a sheet of test material M, such as an air-permeable paper, may be positioned between the jaws. Thereafter, toggle linkage 16 may be suitably manipulated to move the upper jaw 43 downwardly toward the lower jaw, with the jaws sealingly clamping the test material M therebetween. The pressure supplied through conduit 36 is admitted to the interior of the lower jaw so as to be applied across the enclosed 1.0 in$^2$ face of the clamped material.

Such fluid as penetrates the material enters the interior of the upper jaw 43, and is supplied via conduit 44, closed three-position solenoid valve 45, and conduits 46, 48 to the collection means, generally indicated at 49. The pressure in conduit 48 is sensed via conduit 50 by suitable sensing means, such as pressure switch 51. The collection means 49 has a weighted piston 52 therewithin, and includes an expansible chamber 53 arranged to receive fluid from conduit 48. The weight of piston 52 biases chamber 53 to a collapsed or deflated condition. Hence, when the chamber 53 is permitted to vent, as when jaws 38, 43 are open or valve 45 is opened, the weight of piston 52 will exhaust fluid from the chamber. If desired, the collection means may alternatively have a flexible diaphragm or inflatable balloon (not shown). In one preferred form, the inflated volume of chamber 53 is 100 cc, and the pressure switch is appropriately selected to sense this fully-inflated condition.

As previously noted, solenoid switch 45 is of the three-position type, and may be selectively moved or operated to: (1) permit fluid to pass from conduit 44 to conduit 46; (2) block fluid flow between conduits 44 and 46; and (3) vent fluid in conduit 46. When the clamp means 42 is used, valve 45 permits flow between conduits 46 and 48. After an individual test has been completed, valve 45 may be selectively moved to the vent position, thereby allowing the chamber 53 to collapse.

If desired, the apparatus may be designed to accommodate a remote test fixture, generally indicated at 54. Fixture 54 is shown as including stationary cup shaped lower jaw 55, and an inverted mating cup-shaped upper jaw 56 selectively movable toward and away from the lower jaw by means of a toggle linkage 58. From a functional point-of-view, the remote fixture 54 is similar to the integral clamping means 42, except that the cross-sectional area inscribed by the jaws may differ as desired, from that of jaws 38, 43.

To accommodate the option of remote test fixture 54, the apparatus may be further provided with a first conduit 59 having one end communicatively connected to conduit 36, and having a check valve 60 at its other end; and a second conduit 61 having one end communicatively connected to conduit 48 and having a check valve 62 at its other end. A conduit 63 has one end 64 adapted to selectively communicate with conduit 59, and is arranged to supply fluid to the interior of the lower jaw 55. Another conduit 65 has one end 66 adapted to selectively communicate with conduit 61, and is arranged to receive such fluid as may pass through a test material M' to enter the upper jaw. The various connections between conduit ends 64 and 66 with the apparatus, are considered to be a matter of design choice. Functionally, however, check valves 60, 62 are closed when conduit ends 64, 66 are not connected, but are opened when conduit ends 64, 66 are connected. When the remote test fixture 54 is used, jaws 38 and 43 are sealingly closed and valve 45 is moved to its closed position, thereby diverting flow through the remote fixture. The particular cross-sectional area inscribed by remote fixture jaws 55, 56 is also considered to be a matter of design choice.

The filter 28, variable pressure regulator 30 and pressure gauge 24, when connected to the fluid source, collectively constitute supply means, generally indicated at 68, for supplying a flow of fluid at a known test pressure. Solenoid valve 33 comprises valve means operatively arranged between the supply means 68 and lower jaw 38 for selectively permitting the regulated fluid flow to be applied to one face of the material, and for selectively interrupting such flow.

In the aforementioned industry-standard test, the permeability of the material to passage of the fluid is measured in terms of the time needed for 100 cc of the fluid to pass through the 1.0 in$^2$ of the material at a supply pressure of 4.88 inches of water. The various components of the preferred embodiment have been selected for use with this standard test. For example, the supply means 68 is arranged to supply fluid at a regulated pressure of 4.88 inches of water. The clamp means 42 includes two jaws which, when compressed against an interposed specimen of the material, will circumscribe an area of 1.0 in$^2$, to one face of which the regulated pressure will be applied. The inflated volume of the expansible chamber is preferably 100 cc. Hence, if the regulated pressure (4.88 inches of water) is applied to a 1.0 in$^2$ area of a material clamped between jaws 38, 43, such fluid as will pass through the material will be collected in chamber 53, which will inflate to a volume of 100 cc and trigger pressure switch 51.

To calibrate the pneumatic portion of the apparatus, the operator need only close switch 35 and move the jaws into sealed compressive engagement with one another. Thereafter, fluid at the pressure indicated on gauge 24 will be diverted and caused to pass through orifice 40, to subsequently inflate chamber 53. If the inflated volume of chamber 53 is 100 cc, and the orifice is configured to pass fluid at a rate of 100 cc per minute at a supply pressure of 4.88 inches of water, it should take 60 seconds to trigger pressure switch 48. Any deviation in the actual time needed from the nominal time, will indicate a gauge error. Hence, the operator may adjust regulator 30 until the container is inflated in 60 seconds, and calibrate gauge 24 to read 4.88 inches of water at this adjustment. Thereafter, the operator may open valve 35 and begin testing of various specimens of material. As noted above, the area inscribed by the jaws of remote fixture 54 will typically differ from that of jaws 38, 43.

Figure 3:
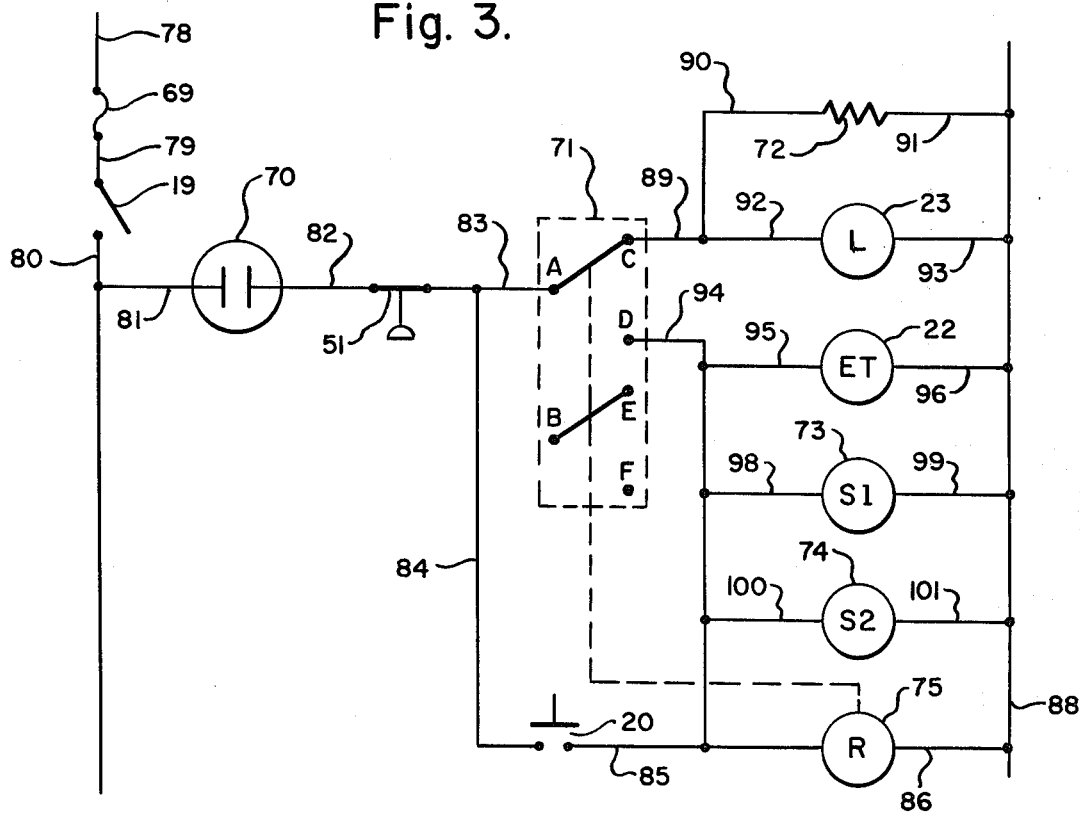
FIG. 3 is a schematic of the electrical circuitry thereof.

The operation of the pneumatic portion of the apparatus is appropriately coupled to the electrical portion, schematically shown in FIG. 3.

Referring now to FIG. 3, the major components of the electrical circuitry include: fuse 69, on-off switch 19; a timer 70, pressure switch 51, relay 71, resistor 72, indicator light 23, elapsed time indicator 22, the coil 73 of solenoid valve 33, the coil 74 of solenoid valve 45, the coil 75 of relay 71, and push button switch 20.

Power is supplied through plug 18 (FIG. 1), conductor 78, fuse 69, conductor 79, switch 19 (when closed) and conductor 80. The timer 70 is connected via conductor 81 to conductor 80, and is connected to the pressure switch 51 via conductor 82. Pressure switch 51 is connected to relay terminal A via conductor 83. A branch circuit includes, in series, conductor 84 connected to conductor 83, push button switch 20, conductor 85, relay coil 75 and conductor 86 connected to common ground 88. If the relay coil is not energized, relay terminals A and C are connected, as shown. Relay terminal C is connected via conductor 89 to two branches arranged in parallel. The first branch includes, in series, conductor 90, resistor 72 and conductor 91 connected to ground wire 88; the second branch includes, in series, conductor 92, light 23 and conductor 93 connected to ground wire 88. When the relay coil 75 is energized, relay terminal A will be electrically connected to relay terminal D, but not to terminal C. Relay terminal D is connected via conductor 94 to conductor 85. A number of branch circuits are arranged in parallel between conductor 94 and ground wire 88. The first of these includes conductor 95, elapsed time indicator 22, and conductor 96; the second includes conductor 98, solenoid relay 73 and conductor 99; and the third includes conductor 100, solenoid relay 74 and conductor 101.

Timer 70 is preferably of the "delay on make"-type. Hence, conductors 81 and 82 are electrically disconnected for a time interval after the apparatus is initially turned on, and immediately following each power interruption. After the timer times out, conductors 81 and 82 are electrically connected.

When the operator initially closes switch 19, and the timer has connected conductors 81 and 82, power will be supplied through the normally-closed pressure switch to relay terminal A. If push button 20 has not been depressed, the relay will be in the condition shown. After passage of the initial time delay, power will pass through relay terminal C to illuminate light 23, thereby indicating a ready condition. In this condition, solenoid coils 73 and 74 are deenergized. This closes valve 33 and vents valve 45, thereby allowing the expansible chamber 53 to collapse. The length of the time delay afforded by the timer should be sufficient to permit the expansible chamber 53 to deflate from a fully-inflated to a fully-deflated condition.

Once the ready light 23 has become illuminated, the operator may clamp a material specimen between jaws 38, 43, and activate the apparatus by depressing push button 20. When this happens, the relay coil 75 will be energized to connect relay terminal A to terminal D instead of terminal C. Ready light 22 is no longer illuminated, but power is simultaneously supplied to elapsed time indicator 22, and solenoid relays 73 and 74. Power in conductor 94 also bypasses the push-button switch, meaning that operation will continue after the operator releases push button 20.

Power in conductor 94 will operate the time totalizer 22, and operate solenoid valve coils 73 and 74. When coil 73 is energized, solenoid valve 33 opens to permit the flow of fluid through conductor 36 to the specimen. At the same time, the energization of coil 74 closes solenoid valve 45 so that such fluid as may pass through the material M will be directed to the expansible chamber 53. Pressure switch 51 will continue to monitor the pressure in conduit 48 as chamber 53 expands.

When chamber 53 has been fully inflated, pressure switch 51 will open to interrupt the supply of power and to restart the delay feature afforded by timer 70. The opening of pressure switch 51 does five things simultaneously: first, time totalizer is deenergized, and continues to visually indicate the time needed to inflate the chamber; secondly, coil 73 is deenergized, thereby again closing valve 33; thirdly, coil 74 is deenergized, thereby opening valve 45 and allowing the fluid in chamber 53 to vent; fourthly, relay coil 75 is deenergized, thereby restoring relay 71 to the condition shown in FIG. 3; and, fifthly, stimulates the timer 70 to afford the time delay feature. As the pressure in chamber 53 falls below that needed to trigger switch 51, switch 51 again closes. However, timer 70 will continue to isolate conductors 82 and 81. As previously noted, the preferred embodiment employs a timer having a delay of sufficient length to allow chamber 53 to resume its fully-deflated condition. After the delay interval has occurred, conductors 81 and 82 will be connected, and ready light 23 will again be illuminated, indicating that the apparatus is in condition for the next sequential test. While the apparatus is disabled by the delay interval, the operator may remove the tested specimen and substitute the next specimen to be tested. As soon as the ready light is again illuminated, the operator need only momentarily depress push button 20 to commence the next test sequence.

In use, the apparatus performs the improved method of measuring the permeability of a material to passage of a fluid, which method comprises the steps of: supplying a flow of fluid at a known test pressure; applying such flow to a known area of the material, collecting such fluid as may pass through the material, and measuring the time interval needed to collect a desired volume of such collected fluid. The improved method may further include one or more of the following additional steps: inflating a collapsible container; sensing the end of the time interval in terms of the pressure within the container, deflating the container after the end of the time interval; or preventing subsequent application of the flow until after the container has been deflated.

Therefore, while a preferred embodiment of the inventive apparatus has been shown and described, persons skilled in this art will readily appreciate that various changes and modifications may be made without departing from the spirit of the invention, as defined by the scope of the following claims.

What is claimed is:

1. The method of measuring the permeability of a material to passage of a fluid, comprising the steps of:
   supplying a flow of said fluid at a desired test pressure;
   applying said flow to a known area of said material;
   collecting such fluid as may pass through said material in an inflatable container;
   sensing the pressure of such fluid in said container; and
   indicating the end of a time interval needed to collect a desired volume of such collected fluid as a function of said sensed pressure.

2. The method as set forth in claim 1, comprising the further step of:
   deflating said collapsible container after the end of said time interval.

3. The method as set forth in claim 1, comprising the further step of:
   preventing subsequent application of said flow until said collapsible container has deflated.

4. Apparatus for measuring the permeability of a material to passage of a fluid, comprising:
   supplying means for supplying a flow of said fluid at a desired test pressure;
   clamp means including a pair of relatively-movable jaws between which a known area of said material may be selectively clamped;
   valve means operatively arranged between said supply means and one of said jaws for selectively permitting said flow to be applied to one face of said material and for selectively interrupting said flow;
   collection means communicatively connected to the other of said jaws and operatively arranged to collect a known volume of such fluid as may pass through said material;
   sensing means operatively arranged to sense the pressure of a desired volume of such fluid within said collection means; and
   timing means operatively arranged to sense the end of a time interval needed to collect said desired volume of such fluid within said collection means as a function of said sensed pressure.

5. The apparatus as set forth in claim 4 wherein said collection means includes a collapsible container arranged to be supplied with such fluid.

6. The apparatus as set forth in claim 5 wherein said sensing means includes a pressure switch operatively arranged to determine when the pressure within said container exceeds a predetermined maximum pressure.

7. The apparatus as set forth in claim 5 wherein said container is in a collapsed condition at the beginning of said time interval and inflated at the end of said time interval.

8. The apparatus as set forth in claim 7 and further comprising: a delay timer for preventing subsequent operation of said valve means until said container has been deflated.

9. The apparatus as set forth in claim 4 wherein said valve means is a solenoid valve.

10. The apparatus as set forth in claim 4 and further comprising: a calibration valve operatively arranged between said valve means and said one jaw, and an orifice of known size arranged in parallel with said calibration valve.

* * * * *